(12) United States Patent
Dugger, III

(10) Patent No.: US 6,969,508 B2
(45) Date of Patent: Nov. 29, 2005

(54) BUCCAL, POLAR AND NON-POLAR SPRAY OR CAPSULE CONTAINING DRUGS FOR TREATING PAIN

(75) Inventor: Harry A. Dugger, III, Flemington, NJ (US)

(73) Assignee: NovaDel Pharma, Inc., Flemington, NJ (US)

( * ) Notice: Subject to any disclaimer, the term of this patent is extended or adjusted under 35 U.S.C. 154(b) by 0 days.

(21) Appl. No.: 10/726,625

(22) Filed: Dec. 4, 2003

(65) Prior Publication Data

US 2004/0120896 A1 Jun. 24, 2004

Related U.S. Application Data

(60) Division of application No. 10/230,059, filed on Aug. 29, 2002, which is a continuation-in-part of application No. 09/537,118, filed on Mar. 29, 2000, which is a continuation-in-part of application No. PCT/US97/17899, filed on Oct. 1, 1997.

(51) Int. Cl.$^7$ .............................. A61K 9/12; A61K 9/08
(52) U.S. Cl. .......................... 424/45; 424/434; 424/435
(58) Field of Search .......................... 424/45, 435, 434, 424/46, 43, 52; 514/772.6, 781, 782; 128/200.14

(56) References Cited

U.S. PATENT DOCUMENTS

| | | | |
|---|---|---|---|
| 3,155,574 A | 11/1964 | Silson et al. ................. 167/54 |
| 3,304,230 A | 2/1967 | Abramson et al. ............ 167/82 |
| 3,784,684 A | 1/1974 | Bossert et al. ................ 424/37 |
| 4,232,002 A | 11/1980 | Nogrady ....................... 424/25 |
| 4,689,233 A | 8/1987 | Dvorsky et al. ............ 424/455 |
| 4,755,389 A | 7/1988 | Jones et al. ................. 424/456 |
| 4,857,312 A | 8/1989 | Hegasy et al. ................ 424/80 |
| 4,919,919 A | 4/1990 | Aouda et al. ................. 424/45 |
| 4,935,243 A | 6/1990 | Borkan et al. .............. 424/441 |
| 5,011,678 A | 4/1991 | Wang et al. .................. 424/45 |
| 5,047,230 A | 9/1991 | Nagy et al. ................... 424/45 |
| 5,128,132 A | 7/1992 | Parnell ..................... 424/195.1 |
| 5,135,753 A | 8/1992 | Baker et al. ................ 424/435 |
| 5,186,925 A | 2/1993 | Cholcha ...................... 424/43 |
| 5,364,616 A | * 11/1994 | Singer et al. ................. 451/52 |
| 5,370,862 A | 12/1994 | Klokkers-Bethke et al. .. 424/47 |
| 5,428,006 A | 6/1995 | Bechgaard .................... 424/45 |
| 5,456,677 A | 10/1995 | Spector ...................... 604/290 |
| 5,457,100 A | 10/1995 | Daniel ........................ 514/220 |
| 5,474,759 A | 12/1995 | Fassberg et al. .............. 424/45 |
| 5,502,076 A | 3/1996 | Dixit et al. |
| 5,519,059 A | 5/1996 | Sawaya ....................... 514/599 |
| 5,593,684 A | 1/1997 | Baker et al. ................ 208/252 |
| 5,605,674 A | * 2/1997 | Purewal et al. .............. 424/45 |
| 5,635,161 A | 6/1997 | Adjei et al. |
| 5,719,197 A | 2/1998 | Kanios et al. ........... 514/772.6 |
| 5,766,573 A | 6/1998 | Purewal et al. .............. 424/45 |
| 5,869,082 A | 2/1999 | Dugger, III ................ 424/435 |
| 5,908,611 A | 6/1999 | Gottlieb et al. |
| 5,955,098 A | 9/1999 | Dugger, III ................ 424/435 |
| 5,981,591 A | 11/1999 | Deihl ........................ 514/568 |
| 6,071,539 A | 6/2000 | Robinson et al. ........... 424/466 |
| 6,110,486 A | 8/2000 | Dugger, III ................ 424/435 |
| 6,299,900 B1 | 10/2001 | Reed et al. |
| 6,458,842 B1 | 10/2002 | Dickinson et al. |
| 6,676,931 B2 | 1/2004 | Dugger, III. |
| 6,706,255 B2 | 3/2004 | Dickinson et al. |
| 2003/0077227 A1 | 4/2003 | Dugger |
| 2003/0082107 A1 | 5/2003 | Dugger |
| 2003/0211047 A1 | * 11/2003 | Dugger, III ................. 424/45 |
| 2004/0120895 A1 | * 6/2004 | Dugger, III ................. 424/44 |
| 2004/0141923 A1 | 7/2004 | Mohammed |

FOREIGN PATENT DOCUMENTS

| | | |
|---|---|---|
| DE | 3338978 | 5/1984 |
| DE | 3246081 | 6/1984 |
| DE | 40007705 | 9/1991 |
| DE | 4038203 | 6/1992 |
| DE | 4112303 | 10/1992 |
| DE | 4132176 | 4/1993 |
| EP | 0140434 | 5/1985 |
| EP | 0213 108 | 3/1987 |
| EP | 0315960 | 5/1989 |
| EP | 0386700 | 3/1990 |
| EP | 0471161 | 2/1992 |
| EP | 0656206 A1 * | 6/1992 |
| EP | 0504112 | 9/1992 |
| EP | 0605483 | 4/1993 |
| EP | 0557129 | 8/1993 |
| EP | 0656206 | 6/1995 |

(Continued)

OTHER PUBLICATIONS

Rote Liste 1995 "Arzneimitteluerzeichnis des BPI and UFA".

Flemington Pharmaceutical Corporation webpage, www.flemington-pharma.com.

Goodman and Gilman's *The Pharmacological Basis of Therapeutics*, 9$^{th}$ ed., pp. 490.

Goodman and Gilman's *The Pharmacological Basis of Therapeutics*, 9$^{th}$ ed., pp. 496.

Goodman and Gilman's *The Pharmacological Basis of Therapeutics*, 9$^{th}$ ed., pp. 497.

*Primary Examiner*—Gary Kunz
*Assistant Examiner*—Mina Haghighatian
(74) *Attorney, Agent, or Firm*—Dickstein Shapiro Morin & Oshinsky LLP

(57) ABSTRACT

Buccal aerosol sprays or capsules using polar and non-polar solvent have now been developed which provide biologically active compounds for rapid absorption through the oral mucosa, resulting in fast onset of effect. The buccal polar compositions of the invention comprise formulation I: aqueous polar solvent, active compound, and optional flavoring agent; formulation II: aqueous polar solvent, active compound, optionally flavoring agent, and propellant; formulation III: non-polar solvent, active compound, and optional flavoring agent; and formulation IV: non-polar solvent, active compound, optional flavoring agent, and propellant.

13 Claims, 1 Drawing Sheet

FOREIGN PATENT DOCUMENTS

| | | |
|---|---|---|
| EP | 0719549 | 7/1996 |
| EP | 1029536 | 8/2000 |
| FR | 26 33933 | 1/1990 |
| GB | 2082457 | 3/1982 |
| WO | WO 90/01046 | 2/1990 |
| WO | WO93/04671 | 3/1993 |
| WO | WO 9413280 * | 6/1994 |
| WO | WO94/13280 | 6/1994 |
| WO | WO95/24893 | 9/1995 |
| WO | WO 99/16417 | 1/1997 |
| WO | WO 97/38662 | 10/1997 |
| WO | WO 97/38663 | 10/1997 |
| WO | WO 97/38687 | 10/1997 |
| WO | WO 98/29097 | 12/1997 |
| WO | WO 00/27359 | 11/1999 |
| WO | WO 00/62757 | 10/2000 |
| WO | WO 01/66089 | 9/2001 |
| WO | WO 02/094232 | 11/2002 |

* cited by examiner

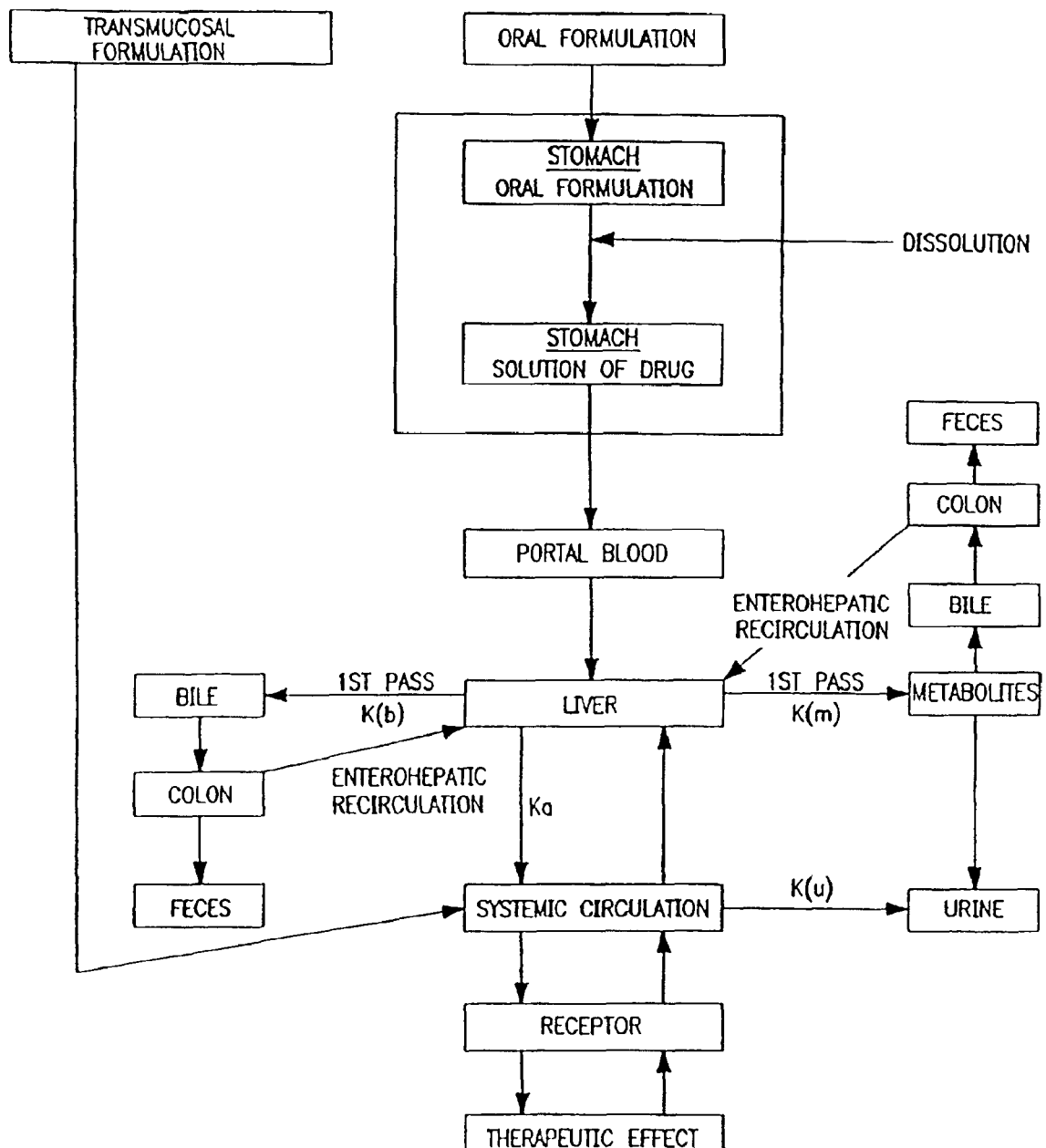

BUCCAL, POLAR AND NON-POLAR SPRAY OR CAPSULE CONTAINING DRUGS FOR TREATING PAIN

CROSS REFERENCE TO RELATED APPLICATIONS

This application is a divisional of U.S. application Ser. No. 10/230,059, filed Aug. 29, 2002, which is a continuation-in-part of application Ser. No. 09/537,118, filed Mar. 29, 2000 which is a continuation-in-part of the U.S. national phase designation of PCT/US97/17899 filed Oct. 1, 1997, the disclosures of which are incorporated by reference herein in their entirety.

BACKGROUND OF THE INVENTION

It is known that certain biologically active compounds are better absorbed through the oral mucosa than through other routes of administration, such as through the stomach or intestine. However, formulations suitable for such administration by these latter routes present their own problems. For example, the biologically active compound must be compatible with the other components of the composition such as propellants, solvents, etc. Many such formulations have been proposed. For example, U.S. Pat. No. 4,689,233, Dvorsky et al., describes a soft gelatin capsule for the administration of the anti-coronary drug nifedipine dissolved in a mixture of polyether alcohols. U.S. Pat. No. 4,755,389, Jones et al., describes a hard gelatin chewable capsule containing nifedipine. A chewable gelatin capsule containing a solution or dispersion of a drug is described in U.S. Pat. No. 4,935,243, Borkan et al. U.S. Pat. No. 4,919,919, Aouda et al, and U.S. Pat. No. 5,370,862, Klokkers-Bethke, describe a nitroglycerin spray for administration to the oral mucosa comprising nitroglycerin, ethanol, and other components. An orally administered pump spray is described by Cholcha in U.S. Pat. No. 5,186,925. Aerosol compositions containing a hydrocarbon propellant and a drug for administration to a mucosal surface are described in U.K. 2,082,457, Su, U.S. Pat. No. 3,155,574, Silson et al., U.S. Pat. No. 5,011,678, Wang et al., and by Parnell in U.S. Pat. No. 5,128,132. It should be noted that these references discuss bioavailability of solutions by inhalation rather than through the membranes to which they are administered.

SUMMARY OF THE INVENTION

A buccal aerosol spray or soft bite gelatin capsule using a polar or non-polar solvent has now been developed which provides biologically active compounds for rapid absorption through the oral mucosa, resulting in fast onset of effect.

The buccal aerosol spray compositions of the present invention, for transmucosal administration of a pharmacologically active compound soluble in a pharmacologically acceptable non-polar solvent comprise in weight % of total composition: pharmaceutically acceptable propellant 5–80%, nonpolar solvent 19–85%, active compound 0.05–50%, suitably additionally comprising, by weight of total composition a flavoring agent 0.01–10%. Preferably the composition comprises: propellant 10–70%, non-polar solvent 25–89.9%, active compound 0.01–40%, flavoring agent 1–8%; most suitably propellant 20–70%, non-polar solvent 25–74.75%, active compound 0.25–35%, flavoring agent 2–7.5%.

The buccal polar aerosol spray compositions of the present invention, for transmucosal administration of a pharmacologically active compound soluble in a pharmacologically acceptable polar solvent are also administrable in aerosol form driven by a propellant. In this case, the composition comprises in weight % of total composition: aqueous polar solvent 10–97%, active compound 0.1–25%, suitably additionally comprising, by weight of total composition a flavoring agent 0.05–10% and propellant: 2–10%. Preferably the composition comprises: polar solvent 20–97%, active compound 0.1–15%, flavoring agent 0.1–5% and propellant 2–5%; most suitably polar solvent 25–97%, active compound 0.2–25%, flavoring agent 0.1–2.5% and propellant 2–4%.

The buccal pump spray composition of the present invention, i.e., the propellant free composition, for transmucosal administration of a pharmacologically active compound wherein said active compound is soluble in a pharmacologically acceptable non-polar solvent comprises in weight % of total composition: non-polar solvent 30–99.69%, active compound 0.005–55%, and suitably additionally, flavoring agent 0.1–10%.

The buccal polar pump spray compositions of the present invention, i.e., the propellant free composition, for transmucosal administration of a pharmacologically active compound soluble in a pharmacologically acceptable polar solvent comprises in weight % of total composition: aqueous polar solvent 30–99.69%, active compound 0.001–60%, suitably additionally comprising, by weight of total composition a flavoring agent 0.1–10%. Preferably the composition comprises: polar solvent 37–98.58%, active compound 0.005–55%, flavoring agent 0.5–8%; most suitably polar solvent 60.9–97.06%, active compound 0.01–40%, flavoring agent 0.75–7.5%.

The soft bite gelatin capsules of the present invention for transmucosal administration of a pharmacologically active compound, at least partially soluble in a pharmacologically acceptable non-polar solvent, having charged thereto a fill composition comprise in weight % of total composition: non-polar solvent 4–99.99%, emulsifier 0–20%, active compound 0.01–80%, provided that said fill composition contains less than 10% of water, suitably additionally comprising, by weight of the composition: flavoring agent 0.01–10%. Preferably, the soft bite gelatin capsule comprises: non-polar solvent 21.5–99.975%, emulsifier 0–15%, active compound 0.025–70%, flavoring agent 1–8%; most suitably: nonpolar solvent 28.5–97.9%, emulsifier 0–10%, active compound 0.1–65.0%, flavoring agent 2–6%.

The soft bite polar gelatin capsules of the present invention for transmucosal administration of a pharmacologically active compound, at least partially soluble in a pharmacologically acceptable polar solvent, having charged thereto a composition comprising in weight % of total composition: polar solvent 25–99.89%, emulsifier 0–20%, active compound 0.01–65%, provided that said composition contains less than 10% of water, suitably additionally comprising, by weight of the composition: flavoring agent 01–10%. Preferably, the soft bite gelatin capsule comprises: polar solvent 37–99.95%, emulsifier 0–15%, active compound 0.025–55%, flavoring agent 1–8%; most suitably: polar solvent 44–96.925%, emulsifier 0–10%, active compound 0.075–50%, flavoring agent 2–6%.

It is an object of the invention to coat the mucosal membranes either with extremely fine droplets of spray containing the active compounds or a solution or paste thereof from bite capsules.

It is also an object of the invention to administer to the oral mucosa of a mammalian in need of same, preferably man, by spray or bite capsule, a predetermined amount of a biologically active compound by this method or from a soft gelatin capsule.

A further object is a sealed aerosol spray container containing a composition of the non polar or polar aerosol spray formulation, and a metered valve suitable for releasing from said container a predetermined amount of said composition.

As the propellant evaporates after activation of the aerosol valve, a mist of fine droplets is formed which contains solvent and active compound.

The propellant is a non-Freon material, preferably a $C_{3-8}$ hydrocarbon of a linear or branched configuration. The propellant should be substantially non-aqueous. The propellant produces a pressure in the aerosol container such that under expected normal usage it will produce sufficient pressure to expel the solvent from the container when the valve is activated but not excessive pressure such as to damage the container or valve seals.

The non-polar solvent is a non-polar hydrocarbon, preferably a $C_{7-18}$ hydrocarbon of a linear or branched configuration, fatty acid esters, and triglycerides, such as miglyol. The solvent must dissolve the active compound and be miscible with the propellant, i.e., solvent and propellant must form a single phase at a temperature of 0–40° C. a pressure range of between 1–3 atm.

The polar and non-polar aerosol spray compositions of the invention are intended to be administered from a sealed, pressurized container. Unlike a pump spray, which allows the entry of air into the container after every activation, the aerosol container of the invention is sealed at the time of manufacture. The contents of the container are released by activation of a metered valve, which does not allow entry of atmospheric gasses with each activation. Such containers are commercially available.

A further object is a pump spray container containing a composition of the pump spray formulation, and a metered valve suitable for releasing from said container a predetermined amount of said composition.

A further object is a soft gelatin bite capsule containing a composition of as set forth above. The formulation may be in the form of a viscous solution or paste containing the active compounds. Although solutions are preferred, paste fills may also be used where the active compound is not soluble or only partially soluble in the solvent of choice. Where water is used to form part of the paste composition, it should not exceed 10% thereof. (All percentages herein are by weight unless otherwise indicated.)

The polar or non-polar solvent is chosen such that it is compatible with the gelatin shell and the active compound. The solvent preferably dissolves the active compound. However, other components wherein the active compound is not soluble or only slightly soluble may be used and will form a paste fill.

Soft gelatin capsules are well known in the art. See, for example, U.S. Pat. No. 4,935,243, Borkan et al., for its teaching of such capsules. The capsules of the present invention are intended to be bitten into to release the low viscosity solution or paste therein, which will then coat the buccal mucosa with the active compounds. Typical capsules, which are swallowed whole or bitten and then swallowed, deliver the active compounds to the stomach, which results in significant lag time before maximum blood levels can be achieved or subject the compound to a large first pass effect. Because of the enhanced absorption of the compounds through the oral mucosa and no chance of a first pass effect, use of the bite capsules of the invention will eliminate much of the lag time, resulting in hastened onset of biological effect. The shell of a soft gelatin capsule of the invention may comprise, for example: gelatin: 50–75%, glycerin 20–30%, colorants 0.5–1.5%, water 5–10%, and sorbitol 2–10%.

The active compound may include, biologically active peptides, central nervous system active amines, sulfonyl ureas, antibiotics, antifungals, antivirals, sleep inducers, antiasthmatics, bronchial dilators, antiemetics, histamine H-2 receptor antagonists, barbiturates, prostaglandins and neutraceuticals.

The active compounds may also include antihistamines, alkaloids, hormones, benzodiazepines and narcotic analgesics. While not limited thereto, these active compounds are particularly suitable for non-polar pump spray formulation and application.

The active compounds may also include nerve impulse inhibitors, anti-opioid agents, anti-migraine agents, anti-muscle spasm agents, pain control agents, anesthetics, anti-inflammatory drugs, or mixtures thereof.

BRIEF DESCRIPTION OF THE DRAWING

FIG. 1, is a schematic diagram showing routes of absorption and processing of pharmacologically active substances in a mammalian system.

DESCRIPTION OF THE PREFERRED EMBODIMENTS

The preferred active compounds of the present invention are in an ionized, salt form or as the free base of the pharmaceutically acceptable salts thereof (provided, for the aerosol or pump spray compositions, they are soluble in the spray solvent). These compounds are soluble in the non-polar solvents of the invention at useful concentrations or can be prepared as pastes at useful concentrations. These concentrations may be less than the standard accepted dose for these compounds since there is enhanced absorption of the compounds through the oral mucosa. This aspect of the invention is especially important when there is a large (40–99.99%) first pass effect.

As propellants for the non polar sprays, propane, N-butane, iso-butane, N-pentane, iso-pentane, and neo-pentane, and mixtures thereof may be used. N-butane and iso-butane, as single gases, are the preferred propellants. It is permissible for the propellant to have a water content of no more than 0.2%, typically 0.1–0.2%. All percentages herein are by weight unless otherwise indicated. It is also preferable that the propellant be synthetically produced to minimize the presence of contaminants which are harmful to the active compounds. These contaminants include oxidizing agents, reducing agents, Lewis acids or bases, and water. The concentration of each of these should be less than 0.1%, except that water may be as high as 0.2%.

Suitable non-polar solvents for the capsules and the non-polar sprays include ($C_2$–$C_{24}$) fatty acid ($C_2$–$C_6$) esters, $C_7$–$C_{18}$ hydrocarbon, $C_2$–$C_6$ alkanoyl esters, and the triglycerides of the corresponding acids. When the capsule fill is a paste, other liquid components may be used instead of the above low molecular weight solvents. These include soya oil, corn oil, other vegetable oils.

As solvents for the polar capsules or sprays there may be used low molecular weight polyethyleneglycols (PEG) of 400–1000 Mw (preferably 400–600), low molecular weight ($C_2$–$C_8$) mono and polyols and alcohols of $C_7$–$C_{18}$ linear or branch chain hydrocarbons, glycerin may also be present and water may also be used in the sprays, but only in limited amount in the capsules.

It is expected that some glycerin and water used to make the gelatin shell will migrate from the shell to the fill during the curing of the shell. Likewise, there may be some migration of components from the fill to the shell during curing and even throughout the shelf-life of the capsule.

Therefore, the values given herein are for the compositions as prepared, it being within the scope of the invention that minor variations will occur.

The preferred flavoring agents are synthetic or natural oil of peppermint, oil of spearmint, citrus oil, fruit flavors, sweeteners (sugars, aspartame, saccharin, etc.), and combinations thereof.

The active substances include the active compounds selected from the group consisting of cyclosporine, sermorelin, octreotide acetate, calcitonin-salmon, insulin lispro, sumatriptan succinate, clozepine, cyclobenzaprine, dexfenfluramine hydrochloride, glyburide, zidovudine, erythromycin, ciprofloxacin, ondansetron hydrochloride, dimenhydrinate, cimetidine hydrochloride, famotidine, phenytoin sodium, phenytoin, carboprost thromethamine, carboprost, diphenhydramine hydrochloride, isoproterenol hydrochloride, terbutaline sulfate, terbutaline, theophylline, albuterol sulfate and neutraceuticals, that is to say nutrients with pharmacological action such as but not limited to camitine, valerian, echinacea, and the like.

In another embodiment, the active compound is a nerve impulse inhibitor, anti-opioid agent, anti-migraine agent, anti-muscle spasm agent, pain control agent, anesthetic, anti-inflammatory drug, or a mixture thereof.

In one embodiment the active compound is a nerve impulse inhibitor. Suitable nerve impulse inhibitors for use in the buccal sprays of the invention include, but are not limited to levobupivacaine, lidocaine, prilocaine, mepivacaine, propofol, rapacuronium bromide, ropivacaine, tubocurarine, atracurium, doxacurium, mivacurium, pancuronium, vecuronium, pipecuronium, rocuronium, and mixtures thereof.

In one embodiment the active compound is an anti-opioid agent. Suitable anti-opioid agents for use in the buccal sprays of the invention include, but are not limited to, naloxone, nalmefene, naltrexone, cholecystokinin, nociceptin, neuropeptide FF, oxytocin, vasopressin, and mixtures thereof.

In one embodiment the active compound is an anti-migraine agent. Suitable anti-migraine agents for use in the buccal sprays of the invention include, but are not limited to, frovatriptan, zolmitriptan, rizatriptan, almotriptan, eletriptan, naratriptan, almotriptan, ergotamine, diethylergotamine, sumatriptan, and mixtures thereof.

In one embodiment the active compound is an anti-muscle spasm agent. Suitable anti-muscle spasm agents for use in the buccal sprays of the invention include, but are not limited to, baclofen, botulinum toxin, carisoprodol, chlorphenesin, chlorzoxazone, cyclobenzaprine, dantrolene, diazepam, metaxalone, methocarbamol, orphenadrine, tizanidine, and mixtures thereof.

In one embodiment the active compound is a pain control agent. Suitable pain control agents for use in the buccal sprays of the invention include, but are not limited to, non-steroidal anti-inflammatory drugs, alfentanil, butorphanol, codeine, dezocine, fentanyl, hydrocodone, hydromorphone, levorphanol, meperidine, methadone, morphine, nalbuphine, oxycodone, oxymorphone, propoxyphene, pentazocine, sufentanil, tramadol, and mixtures thereof.

In one embodiment the active compound is an anesthetic. Suitable anesthetics for use in the buccal sprays of the invention include, but are not limited to, benzonatate, bupivacaine, desflurane, enflurane, isoflurane, levobupivacaine, lidocaine, mepivacaine, prilocaine, propofol, rapacuronium bromide, ropivacaine, sevoflurane, ketamine, and mixtures thereof.

In one embodiment the active compound is an anti-inflammatory drug. Suitable anti-inflammatory drugs for use in the buccal sprays of the invention include, but are not limited to, alosetron, anakinra, beclomethasone, betamethasone, budesonide, clobetasol, celecoxib, cromolyn, desoximetasone, dexamethasone, epinastic, etanercept, etoricoxib, flunisolide, fluocinonide, fluticasone, formoterol, hydrocortisone, hydroxychloroquine, ibudilast, ketotifen, meloxicam, mesalamine, methotrexate, methylprednisolone, mometasone, montelukast, nedocromil, olsalazine, prednisone, ramatroban, rofecoxib, salsalate, terbutaline, triamcinolone, valdecoxib, zafirlukast, and mixtures thereof.

The formulations of the present invention comprise an active compound or a pharmaceutically acceptable salt thereof. The term "pharmaceutically acceptable salts" refers to salts prepared from pharmaceutically acceptable non-toxic acids or bases including organic and inorganic acids or bases.

When an active compound of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N dibenzylethylenediamine, diethylamine, 2-diethylaminoethanol, 2-dimethyl-aminoethanol, ethanolamine, ethylenediamine, N-ethylmorpholine, N-ethylpiperidine, glucamine, glucosamine, histidine, isopropylamine, lysine, methyl-glucosamine, morpholine, piperazine, piperidine, polyamine resins, procaine, purine, theobromine, triethylamine, trimethylamine, tripropylamine, etc.

When an active compound of the present invention is basic, salts may be prepared from pharmaceutically acceptable non-toxic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Particularly preferred are citric, hydrobromic, maleic, phosphoric, sulfuric, and tartaric acids.

In the discussion of methods of treatment herein, reference to the active compounds is meant to also include the pharmaceutically acceptable salts thereof. While certain formulations are set forth herein, the actual amounts to be administered to the mammal or man in need of same are to be determined by the treating physician.

The invention is further defined by reference to the following examples, which are intended to be illustrative and not limiting.

The following are examples of certain classes. All values unless otherwise specified are in weight percent.

EXAMPLES

Example 1

Biologically active peptides including peptide hormones

A. Cyclosporine lingual spray

|  | Amounts | preferred amount | most preferred amount |
|---|---|---|---|
| cyclosporine | 5–50 | 10–35 | 15–25 |
| water | 5–20 | 7.5–50 | 9.5–12 |
| ethanol | 5–60 | 7.5–50 | 10–20 |
| polyethylene glycol | 20–60 | 30–45 | 35–40 |
| flavors | 0.1–5 | 1–4 | 2–3 |

B. Cyclosporine Non-Polar lingual spray

|  | Amounts | preferred amount | most preferred amount |
|---|---|---|---|
| cyclosporine | 1–50 | 3–40 | 5–30 |
| Migylol | 20 | 25 | 30–40 |
| Polyoxyethylated castor oil | 20 | 25 | 30–40 |
| Butane | 25–80 | 30–70 | 33–50 |
| flavors | 0.1–5 | 1–4 | 2–3 |

C. Cyclosporine non-polar bite caosule

|  | Amounts | preferred amount | most preferred amount |
|---|---|---|---|
| cyclosporine | 1–35 | 5–25 | 10–20 |
| olive oil | 25–60 | 35–55 | 30–45 |
| polyoxyethylated oleic glycerides | 25–60 | 35–55 | 30–45 |
| flavors | 0.1–5 | 1–4 | 2–3 |

D. Cyclosporine bite capsule

|  | Amounts | preferred amount | most preferred amount |
|---|---|---|---|
| cyclosporine | 5–50 | 10–35 | 15–25 |
| polyethylene glycol | 20–60 | 30–45 | 35–40 |
| glycerin | 5–30 | 7.5–25 | 10–20 |
| propylene glycol | 5–30 | 7.5–25 | 10–20 |
| flavors | 0.1–10 | 1–8 | 3–6 |

E. Sermorelin (as the acetate) lingual spray

|  | Amounts | preferred amount | most preferred |
|---|---|---|---|
| sermorelin (as the acetate) | .01–5 | .1–3 | .2–1.0 |
| mannitol | 1–25 | 5–20 | 10–15 |
| monobasic sodium phosphate, | 0.1–5 | 1–31 | .5–2.5 |
| dibasic sodium phosphate water | 0.01–5 | .05–3 | 0.1–0.5 |
| ethanol | 5–30 | 7.5–25 | 9.5–15 |
| polyethylene glycol | 20–60 | 30–45 | 35–40 |
| propylene glycol | 5–25 | 10–20 | 12–17 |
| flavors | 0.1–5 | 1–4 | 2–3 |

F. Octreotide acetate (Sandostatin) lingual spray

|  | Amounts | preferred amount | most preferred amount |
|---|---|---|---|
| octreotide acetate | 0.001–0.5 | 0.005–0.250 | 0.01–0.10 |
| acetic acid | 1–10 | 2–8 | 4–6 |
| sodium acetate | 1–10 | 2–8 | 4–6 |
| sodium chloride | 3–30 | .5–25 | 15–20 |
| flavors | 0.1–5 | 0.5–.4 | 2–3 |
| ethanol | 5–30 | 7.5–20 | 9.5–15 |
| water | 15–95 | 35–90 | 65–85 |
| flavors | 0.1–5 | 1–4 | 2–3 |

G. Calcitonin-salmon lingual spray

|  | Amounts | preferred amount | most preferred amount |
|---|---|---|---|
| calcitonin-salmon | 0.001–5 | 0.005–2 | 01–1.5 |
| ethanol | 2–15 | 3–10 | 7–9.5 |
| water | 30–95 | 50–90 | 60–80 |
| polyethylene glycol | 2–15 | 3–10 | 7–9.5 |
| sodium chloride | 2.5–20 | 5–15 | 10–12.5 |
| flavors | 0.1–5 | 1–4 | 2–3 |

H. Insulin lispro, lingual spray

|  | Amounts | preferred amount | most preferred amount |
|---|---|---|---|
| insulin | 20–60 | 4–55 | 5–50 |
| glycerin | 0.1–10 | 0.25–5 | 0.1–1.5 |
| dibasic sodium phosphate | 1–15 | 2.5–10 | 4–8 |
| m-cresol, | 1–25 | 5–25 | 7.5–12.5 |
| zinc oxide | 0.01–0.25 | .05–0.15 | 0.075–0.10 |
| m-cresol | 0.1–1 | 0.2–0.8 | 0.4–0.6 |
| phenol | trace amounts | trace amounts | trace amounts |
| ethanol | 5–20 | 7.5–15 | 9–12 |
| water | 30–90 | 40–80 | 50–75 |
| propylene glycol | 5–20 | 7.5–15 | 9–12 |
| flavors | 0.1–5 | 0.5–3 | 0.75–2 | adjust pH to 7.0–7.8 with HCl or NaOH

Example 2

CNS active amines and their salts: including but not limited to tricyclic amines, GABA analogues, thiazides, phenothiazine derivatives, serotonin antagonists and serotonin reuptake inhibitors

A. Sumatriptan succinate lingual spray

|  | Amounts | preferred amount | most preferred amount |
|---|---|---|---|
| sumatriptan succinate | 0.5–30 | 1–20 | 10–15 |
| ethanol | 5–60 | 7.5–50 | 10–20 |
| propylene glycol | 5–30 | 7.5–20 | 10–15 |
| polyethylene glycol | 0–60 | 30–45 | 35–40 |
| water | 5–30 | 7.5–20 | 10–15 |
| flavors | 0.1–5 | 1–4 | 2–3 |

B. Sumatriptan succinate bite capsule

|  | Amounts | preferred amount | most preferred amount |
|---|---|---|---|
| sumatriptan succinate | 0.01–5 | 0.05–3.5 | 0.075–1.75 |
| polyethylene glycol | 25–70 | 30–60 | 35–50 |
| glycerin | 25–70 | 30–60 | 35–50 |
| flavors | 0.1–10 | 1–8 | 3–6 |

C. Clozepine lingual spray

|  | Amounts | preferred amount | most preferred amount |
|---|---|---|---|
| clozepine | 0.5–30 | 1–20 | 10–15 |
| ethanol | 5–60 | 7.5–50 | 10–20 |
| propylene glycol | 5–30 | 7.5–20 | 10–15 |
| polyethylene glycol | 0–60 | 30–45 | 35–40 |
| water | 5–30 | 7.5–20 | 10–15 |
| flavors | 0.1–5 | 1–4 | 2–3 |

D. Clozepine non-polar lingual spray with propellant

|  | Amounts | preferred amount | most preferred amount |
|---|---|---|---|
| clozepine | 0.5–30 | 1–20 | 10–15 |
| Migylol | 20–85 | 25–70 | 30–40 |
| Butanol | 5–80 | 30–75 | 60–70 |
| flavors | 0.1–5 | 1–4 | 2–3 |

E. Clozepine non-polar lingual spray without propellant

|  | Amounts | preferred amount | most preferred amount |
|---|---|---|---|
| clozepine | 0.5–30 | 1–20 | 10–15 |
| Migylol | 70–99.5 | 80–99 | 85–90 |
| flavors | 0.1–5 | 1–4 | 2–3 |

F. Cyclobenzaprine non-polar lingual spray

|  | Amounts | preferred amount | most preferred amount |
|---|---|---|---|
| cyclobenzaprine (base) | 0.5–30 | 1–20 | 10–15 |
| Migylol | 20–85 | 25–70 | 30–40 |
| Iso-butane | 15–80 | 30–75 | 60–70 |
| flavors | 0.1–5 | 1–4 | 2–3 |

G. Dexfenfluramine hydrochloride lingual spray

|  | Amounts | preferred amount | most preferred amount |
|---|---|---|---|
| dexfenfluramine Hcl | 5–30 | 7.5–20 | 10–15 |
| ethanol | 5–60 | 7.5–50 | 10–20 |
| propylene glycol | 5–30 | 7.5–20 | 10–15 |
| polyethylene glycol | 0–60 | 30–45 | 35–40 |
| water | 5–30 | 7.5–20 | 10–15 |
| flavors | 0.1–5 | 1–4 | 2–3 |

Example 3

Sulfonylureas

A. Glyburide lingual spray

|  | Amounts | preferred amount | most preferred amount |
|---|---|---|---|
| glyburide | 0.25–25 | 0.5–20 | 0.75–15 |
| ethanol | 5–60 | –7.5–50 | 10–20 |
| propylene glycol | 5–30 | 7.5–20 | 10–15 |
| polyethylene glycol | 0–60 | 30–45 | 35–40 |
| water | 2.5–30 | 5–20 | 6–15 |
| flavors | 0.1–5 | 1–4 | 2–3 |

B. Glyburide non-polar bite capsule

|  | Amounts | preferred amount | most preferred amount |
|---|---|---|---|
| glyburide | 0.01–10 | 0.025–7.5 | 0.1–4 |
| olive oil | 30–60 | 35–55 | 30–50 |
| polyoxyethylated oleic glycerides | 30–60 | 35–55 | 30–50 |
| flavors | 0.1–5 | 1–4 | 2–3 |

Example 4

Antibiotics anti-fungals and anti-virals

A. Zidovudine [formerly called azidothymidine (AZT) (Retrovir)] non-polar lingual spray

|  | Amounts | preferred amount | most preferred amount |
|---|---|---|---|
| zidovudine | 10–50 | 15–40 | 25–35 |
| Soya oil | 20–85 | 25–70 | 30–40 |

-continued

A. Zidovudine [formerly called azidothymidine (AZT) (Retrovir)] non-polar lingual spray

|  | Amounts | preferred amount | most preferred amount |
|---|---|---|---|
| Butane | 15–80 | 30–75 | 60–70 |
| flavors | 0.1–5 | 1–4 | 2–3 |

B. Erythromycin bite capsule bite capsule

|  | Amounts | preferred amount | most preferred amount |
|---|---|---|---|
| erythromycin | 25–65 | 30–50 | 35–45 |
| polyoxyethylene glycol | 5–70 | 30–60 | 45–55 |
| glycerin | 5–20 | 7.5–15 | 10–12.5 |
| flavors | 1–10 | 2–8 | 3–6 |

C. Ciprofloxacin hydrochloride bite capsule

|  | Amounts | preferred amount | most preferred amount |
|---|---|---|---|
| ciprofloxacin hydrochloride | 25–65 | 35–55 | 40–50 |
| glycerin | 5–20 | 7.5–15 | 10–12.5 |
| polyethylene glycol | 120–75 | 30–65 | 40–60 |
| flavors | 1–10 | 2–8 | 3–6 |

D. zidovudine [formerly called azidothymidine (AZT) (Retrovir)] lingual spray

|  | Amounts | preferred amount | most preferred amount |
|---|---|---|---|
| zidovudine | 10–50 | 15–40 | 25–35 |
| water | 30–80 | 40–75 | 45–70 |
| ethanol | 5–20 | 7.5–15 | 9.5–12.5 |
| polyethylene glycol | 5–20 | 7.5–15 | 9.5–12.5 |
| flavors | 0.1–5 | 1–4 | 2–3 |

Example 5

Anti-Emetics

A. Ondansetron hydrochloride lingual spray

|  | Amounts | preferred amount | most preferred amount |
|---|---|---|---|
| ondansetron hydrochloride | 1–25 | 2–20 | 2.5–15 |
| citric acid monohydrate | 1–10 | 2–8 | 2.5–5 |
| sodium citrate dihydrate | 0.5–5 | 1–4 | 1.25–2.5 |
| water | 1–90 | 5–85 | 10–75 |
| ethanol | 5–30 | 7.5–20 | 9.5–15 |
| propylene glycol | 5–30 | 7.5–20 | 9.5–15 |
| polyethylene glycol | 5–30 | 7.5–20 | 9.5–15 |
| flavors | 1–10 | 3–8 | 5–7.5 |

B. Dimenhydrinate bite capsule

|  | Amounts | preferred amount | most preferred amount |
|---|---|---|---|
| dimenhydrinate | 0.5–30 | 2–25 | 3–15 |
| glycerin | 5–20 | 7.5–15 | 10–12.5 |
| polyethylene glycol | 45–95 | 50–90 | 55–85 |
| flavors | 1–10 | 2–8 | 3–6 |

C. Dimenhydrinate polar lingual spray

|  | Amounts | preferred amount | most preferred amount |
|---|---|---|---|
| dimenhydrinate | 3–50 | 4–40 | 5–35 |
| water | 5–90 | 10–80 | 15–75 |
| ethanol | 1–80 | 3–50 | 5–10 |
| polyethylene glycol | 1–80 | 3–50 | 5–15 |
| sorbitol | 0.1–5 | 0.2–40 | 0.4–1.0 |
| aspartame | 0.01–0.5 | 0.02–0.4 | 0.04–0.1 |
| flavors | 0.1–5 | 1–4 | 2–3 |

Example 6

Histamine H-2 Receptor Antagonists

A. Cimetidine hydrochloride bite capsule

|  | Amounts | preferred amount | most preferred amount |
|---|---|---|---|
| cimetidine HCl | 10–60 | 15–55 | 25–50 |
| glycerin | 5–20 | 7.5–15 | 10–12.5 |
| polyethylene glycol | 20–90 | 25–85 | 30–75 |
| flavors | 1–10 | 2–8 | 3–6 |

B. Famotidine lingual spray

|  | Amounts | preferred amount | most preferred amount |
|---|---|---|---|
| famotidine | 1–35 | 5–30 | 7–20 |
| water | 2.5–25 | 3–20 | 5–10 |
| L-aspartic acid | 0.1–20 | 1–15 | 5–10 |
| polyethylene glycol | 20–97 | 30–95 | 50–85 |
| flavors | 0.1–10 | 1–7.5 | 2–5 |

C. Famotidine non-polar lingual spray

|  | Amounts | preferred amount | most preferred amount |
|---|---|---|---|
| famotidine | 1–35 | 5–30 | 7–20 |
| Soya oil | 10–50 | 15–40 | 15–20 |
| Butane 1 | 5–80 | 30–75 | 45–70 |
| polyoxyethylated oleic glycerides | 10–50 | 15–40 | 15–20 |
| flavors | 0.1–5 | 1–4 | 2–3 |

Example 7

Barbiturates

A. Phenytoin sodium lingual spray

|  | Amounts | preferred amount | most preferred amount |
|---|---|---|---|
| phenytoin sodium | 10–60 | 15–55 | 20–40 |
| water | 2.5–25 | 3–20 | 5–10 |
| ethanol | 5–30 | 7.5–20 | 9.5–15 |
| propylene glycol | 5–30 | 7.5–20 | 9.5–15 |
| polyethylene glycol | 5–30 | 7.5–20 | 9.5–15 |
| flavors | 1–10 | 3–8 | 5–7.5 |

B. Phenytoin non-polar lingual spray

|  | Amounts | preferred amount | most preferred amount |
|---|---|---|---|
| phenytoin | 5–45 | 10–40 | 15–35 |
| migylol | 10–50 | 15–40 | 15–20 |
| Butane | 15–80 | 30–75 | 60–70 |
| polyoxyethylated oleic glycerides | 10–50 | 15–40 | 15–20 |
| flavors | 0.1–10 | 1–8 | 5–7.5 |

Example 8

Prostaglandins

A. Carboprost thromethamine lingual spray

|  | Amounts | preferred amount | most preferred amount |
|---|---|---|---|
| carboprost thromethamine | 0.05–5 | 0.1–3 | 0.25–2.5 |
| water | 50–95 | 60–80 | 65–75 |
| ethanol | 5–20 | 7.5–15 | 9.5–12.5 |
| polyethylene glycol | 5–20 | 7.5–15 | 9.5–12.5 |
| sodium chloride | 1–20 | 3–15 | 4–8 |
| flavors | 0.1–5 | 1–4 | 2–3 | pH is adjusted with sodium hydroxide and/or hydrochloric acid

B. Carboprost non-polar lingual spray

|  | Amounts | preferred amount | most preferred amount |
|---|---|---|---|
| carboprost | 0.05–5 | 0.1–3 | 0.25–2.5 |
| migylol | 25–50 | 30–45 | 35–40 |
| Butane | 5–60 | 10–50 | 20–35 |
| polyoxyethylated oleic glycerides | 25–50 | 30–45 | 35–40 |
| flavors | 0.1–10 | 1–8 | 5–7.5 |

Example 9

Neutraceuticals

A. Carnitine as bite capsule (contents are a paste)

|  | Amounts | preferred amount | most preferred amount |
|---|---|---|---|
| carnitine fumarate | 6–80 | 30–70 | 45–65 |
| soya oil | 7.5–50 | 10–40 | 12.5–35 |
| soya lecithin | 0.001–1.0 | 0.005–0.5 | .01–0.1 |
| Soya fats | 7.5–50 | 10–40 | 12.5–35 |
| flavors | 1–10 | 2–8 | 3–6 |

B. Valerian as lingual spray

|  | Amounts | preferred amount | most preferred amount |
|---|---|---|---|
| valerian extract | 0.1–10 | 0.2–7 | 0.25–5 |
| water | 50–95 | 60–80 | 65–75 |
| ethanol | 5–20 | 7.5–15 | 9.5–12.5 |
| polyethylene glycol | 5–20 | 7.5–15 | 9.5–12.5 |
| flavors | 1–10 | 2–8 | 3–6 |

C. Echinacea as bite capsule

|  | Amounts | preferred amount | most preferred amount |
|---|---|---|---|
| echinacea extract | 30–85 | 40–75 | 45–55 |
| soya oil | 7.5–50 | 10–40 | 12.5–35 |
| soya lecithin | 0.001–1.0 | 0.005–0.5 | .01–0.1 |
| Soya fats | 7.5–50 | 10–40 | 12.5–35 |
| flavors | 1–10 | 2–8 | 3–6 |

D. Mixtures of ingredients

|  | Amounts | preferred amount | most preferred amount |
|---|---|---|---|
| magnesium oxide | 15–40 | 20–35 | 25–30 |
| chromium picolinate | 0.01–1.0 | 0.02–0.5 | .025–0.75 |
| folic acid | .025–3.0 | 0.05–2.0 | 0.25–0.5 |
| vitamin B-12 | 0.01–1.0 | 0.02–0.5 | .025–0.75 |
| vitamin E | 15–40 | 20–35 | 25–30 |
| Soya oil | 10–40 | 12.5–35 | 15–20 |
| soya lecithin | 0.1–5 | 0.2–4 | 0.5–1.5 |
| soya fat | 10–40 | 15–35 | 17.5–20 |

Example 10

Sleep Inducers (also CNS active amine)

A. Diphenhydramine hydrochloride lingual spray

|  | Amounts | preferred amount | most preferred amount |
|---|---|---|---|
| diphenhydramine HCl | 3–50. | 4–40 | 5–35 |
| water | 5–90 | 10–80 | 50–75 |
| ethanol | 1–80 | 3–50 | 5–10 |

-continued

A. Diphenhydramine hydrochloride lingual spray

|  | Amounts | preferred amount | most preferred amount |
|---|---|---|---|
| polyethylene glycol | 1–80 | 3–50 | 5–15 |
| Sorbitol | 0.1–5 | 0.2–4 | 0.4–1.0 |
| aspartame | 0.01–0.5 | 0.02–0.4 | 0.04–0.1 |
| flavors | 0.1–5 | 1–4 | 2–3 |

Example 11

Anti-Asthmatics-Bronchodilators

A. Isoproterenol Hydrochloride as polar lingual spray

|  | Amounts | preferred amount | most preferred amount |
|---|---|---|---|
| isoproterenol Hydrochloride | 0.1–10 | 0.2–7.5 | 0.5–6 |
| water | 5–90 | 10–80 | 50–75 |
| ethanol | 1–80 | 3–50 | 5–10 |
| polyethylene glycol | 1–80 | 3–50 | 5–15 |
| Sorbitol | 0.1–5 | 0.2–4 | 0.4–1.0 |
| aspartame | 0.01–0.5 | 0.02–0.4 | 0.04–0.1 |
| flavors | 0.1–5 | 1–4 | 2–3 |

B. Terbutaline sulfate as polar lingual spray

|  | Amounts | preferred amount | most preferred amount |
|---|---|---|---|
| terbutaline sulfate | 0.1–10 | 0.2–7.5 | 0.5–6 |
| water | 5–90 | 10–80 | 50–75 |
| ethanol | 1–10 | 2–8 | 2.5–5 |
| Sorbitol | 0.1–5 | 0.2–4 | 0.4–1.0 |
| aspartame | 0.01–0.5 | 0.02–0.4 | 0.04–0.1 |
| flavors | 0.1–5 | 1–4 | 2–3 |

C. Terbutaline as non-polar lingual spray

|  | Amounts | preferred amount | most preferred amount |
|---|---|---|---|
| terbutaline | 0.1–10 | 0.2–7.5 | 0.5–6 |
| migylol | 25–50 | 30–45 | 35–40 |
| isobutane | 5–60 | 10–50 | 20–35 |
| polyoxyethylated oleic glycerides | 25–50 | 30–45 | 35–40 |
| flavors | 0.1–10 | 1–8 | 5–7.5 |

D. Theophylline polar bite capsule

|  | Amounts | preferred amount | most preferred amount |
|---|---|---|---|
| theophylline | 5–50 | 10–40 | 15–30 |
| polyethylene glycol | 20–60 | 25–50 | 30–40 |
| glycerin | 25–50 | 35–45 | 30–40 |
| propylene glycol | 25–50 | 35–45 | 30–40 |
| flavors | 0.1–5 | 1–4 | 2–3 |

E. Albuterol sulfate as polar lingual spray

|  | Amounts | preferred amount | most preferred amount |
|---|---|---|---|
| albuterol sulfate | 0.1–10 | 0.2–7.5 | 0.5–6 |
| water | 5–90 | 10–80 | 50–75 |
| ethanol | 1–10 | 2–8 | 2.5–5 |
| Sorbitol | 0.1–5 | 0.2–4 | 0.4–1.0 |
| aspartame | 0.01–0.5 | 0.02–0.4 | 0.04–0.1 |
| flavors | 0.1–5 | 1–4 | 2–3 |

Example 12

Polar Solvent Formulations Using a Propellant:

A. Sulfonylurea

|  | Amount | Preferred Amount | Most-Preferred Amount |
|---|---|---|---|
| glyburide | 0.1–25% | 0.5–15% | 0.6–10% |
| Ethanol | 40–99% | 60–97% | 70–97% |
| Water | 0.01–5% | 0.1–4% | 0.2–2% |
| Flavors | 0.05–10% | 0.1–5% | 0.1–2.5% |
| Propellant | 2–10% | 3–5% | 3–4% |

B. Prostaglandin E (vasodilator)

|  | Amount | Preferred Amount | Most-Preferred Amount |
|---|---|---|---|
| prostaglandin $E_1$ | 0.01–10% | 0.1–5% | 0.2–3% |
| Ethanol | 10–90% | 20–75% | 25–50% |
| Propylene glycol | 1–90% | 5–80% | 10–75% |
| Water | 0.01–5% | 0.1–4% | 0.2–2% |
| Flavors | 0.05–10% | 0.1–5% | 0.1–2.5% |
| Propellant | 2–10% | 3–5% | 3–4% |

C. Promethazine (antiemetic, sleep inducer, and CNS active amine)

|  | Amount | Preferred Amount | Most-Preferred Amount |
|---|---|---|---|
| promethazine | 1–25% | 3–15% | 5–12% |
| Ethanol | 10–90% | 20–75% | 25–50% |
| Propylene glycol | 1–90% | 5–80% | 10–75% |
| Water | 0.01–5% | 0.1–4% | 0.2–2% |
| Flavors | 0.05–10% | 0.1–5% | 0.1–2.5% |
| Propellant | 2–10% | 3–5% | 3–4% |

D. Meclizine

|  | Amount | Preferred Amount | Most-Preferred Amount |
|---|---|---|---|
| meclizine | 1–25% | 3–15% | 5–12% |
| Ethanol | 1–15% | 2–10% | 3–6 |
| Propylene glycol | 20–98% | 5–90% | 10–85% |
| Water | 0.01–5% | 0.1–4% | 0.2–2% |

-continued

D. Meclizine

|  | Amount | Preferred Amount | Most-Preferred Amount |
|---|---|---|---|
| Flavors | 0.05–10% | 0.1–5% | 0.1–2.5% |
| Propellant | 2–10% | 3–5% | 3–4% |

What is claimed is:

1. A method for administering an effective amount of a pharmacologically active compound to a mammal to provide transmucosal absorption of a pharmacologically effective amount of the active compound through the oral mucosa of the mammal to the systemic circulatory system of the mammal, comprising:
spraying the oral mucosa of the mammal with a buccal spray composition, containing a pharmacologically active compound dissolved in a pharmacologically acceptable solvent, comprising in weight percent of the composition:
an active compound in an amount of between 0.1 and 25 percent selected from the group consisting of anti-opioid agents, anti-migraine agents, pain control agents, anesthetics, and mixtures thereof;
a polar solvent in an amount between 10 and 97 percent; and
a propellant in an amount between 2 and 10 percent, wherein said propellant is a $C_3$ to $C_8$ hydrocarbon of linear or branched configuration.

2. The method of claim 1, wherein the spray composition further comprises a flavoring agent in an amount between 0.05 and 10 percent by weight of the total composition.

3. The method of claim 2, wherein the polar solvent is present in an amount between 20 and 97 percent by weight of the total composition, the active compound is present in an amount between 0.1 and 15 percent by weight of the total composition, the propellant is present in an amount between 2 and 5 percent by weight of the composition, and the flavoring agent is present in an amount between 0.1 and 5 percent by weight of the total composition.

4. The method of claim 3, wherein the polar solvent is present in an amount between 25 and 97 percent by weight of the total composition, the active compound is present in an amount between 0.2 and 25 percent by weight of the total composition, the propellant is present in an amount between 2 and 4 percent by weight of the composition, and flavoring agent is present in an amount between 0.1 and 2.5 percent by weight of the total composition.

5. The method of claim 1, wherein the polar solvent is selected from the group consisting of polyethyleneglycols having a molecular weight between 400 and 1000, $C_2$ to $C_8$ mono- and poly-alcohols, and $C_7$ to $C_{18}$ alcohols of linear or branched configuration.

6. The method of claim 5, wherein the polar solvent comprises aqueous polyethylene glycol.

7. The method of claim 5, wherein the polar solvent comprises aqueous ethanol.

8. The method of claim 1, wherein the active compound is an anti-opioid agent selected from the group consisting of naloxone, nalmefene, naltrexone, cholecystokinin, nociceptin, neuropeptide FF, oxytocin, vasopressin, and mixtures thereof.

9. The method of claim 1, wherein the active compound is an anti-migraine agent selected from the group consisting of frovatriptan, zolmitriptan, rizatriptan, almotriptan, eletriptan, naratriptan, almotriptan, ergotamine, diethylergotamine, sumatriptan, and mixtures thereof.

10. The method of claim 1, wherein the active compound is a pain control agent selected from the group consisting of non-steroidal anti-inflammatory drugs, alfentanil, butorphanol, codeine, dezocine, fentanyl, hydrocodone, hydromorphone, levorphanol, meperidine, methadone, morphine, nalbuphine, oxycodone, oxymorphone, propoxyphene, pentazocine, sufentanil, tramadol, and mixtures thereof.

11. The method of claim 1, wherein the active compound is an anesthetic selected from the group consisting of benzonatate, bupivacaine, desflurane, enflurane, isoflurane, levobupivacaine, lidocaine, mepivacaine, prilocaine, propofol, rapacuronium bromide, ropivacaine, sevoflurane, ketamine, and mixtures thereof.

12. The method of claim 2, wherein the flavoring agent is selected from the group consisting of synthetic or natural oil of peppermint, oil of spearmint, citrus oil, fruit flavors, sweeteners, and mixtures thereof.

13. The method of claim 1, wherein the propellant is selected from the group consisting of propane, N-butane, iso-butane, N-pentane, iso-pentane, neo-pentane, and mixtures thereof.

* * * * *